US00PP26996P3

(12) United States Plant Patent
Tristram

(10) Patent No.: US PP26,996 P3
(45) Date of Patent: Aug. 2, 2016

(54) ***RHODODENDRON* PLANT NAMED 'WALSNOWRUF'**

(50) Latin Name: ***Rhododendron kaempferi* hybrid**
Varietal Denomination: WALSNOWRUF

(71) Applicant: David Tristram, Arundel (GB)

(72) Inventor: David Tristram, Arundel (GB)

( * ) Notice: Subject to any disclaimer, the term of this patent is extended or adjusted under 35 U.S.C. 154(b) by 147 days.

(21) Appl. No.: 14/120,710

(22) Filed: Jun. 17, 2014

(65) Prior Publication Data

US 2014/0380535 P1 Dec. 25, 2014

Related U.S. Application Data

(60) Provisional application No. 61/956,954, filed on Jun. 20, 2013.

(51) Int. Cl.
*A01H 5/02* (2006.01)

(52) U.S. Cl.
USPC ..... Plt./238
CPC ..... *A01H 5/02* (2013.01)

(58) Field of Classification Search
USPC ..... Plt./238
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A new and distinct variety of *Rhododendron* plant named 'WALSNOWRUF' which is characterized by compact mounding habit, glossy evergreen foliage, large double bright white flowers which are produced from early summer through early fall (July to September approximately), is disclosed.

2 Drawing Sheets

Genus and species: *Rhododendron kaempferi* hybrid.
Variety denomination: 'WALSNOWRUF'.

BACKGROUND OF THE NEW PLANT

The present invention relates to a new and distinct cultivar of *Rhododendron*, also commonly known as evergreen azalea, which is grown as an ornamental shrub for use in planted containers and in the garden and landscape. The new cultivar is known botanically as *Rhododendron kaempferi* hybrid, and will be referred to hereinafter by the cultivar name 'WALSNOWRUF'.

'WALSNOWRUF' arose and was selected from a long term breeding program commenced by the inventor in 1993 or 1994. The aim of the breeding program was to develop one or more matched series of novel cultivars of hardy evergreen azaleas with showy flowers, large open-faced single flowers, and also heavily flowering double flower forms. Breeding commenced with Azalea 'Elsie Lee' as one of the initial parents. Azalea 'Elsie Lee' is a Shammarello hybrid, raised in Ohio in the 1960s and renowned for its fertility and relative hardiness among evergreen azaleas. Although several Shammarello hybrids were patented in the 1960s and 1970s, the inventor believes that Azalea 'Elsie Lee' was unpatented. 'Elsie Lee' bears light mauve-blue semi-double flowers.

Commencing in 1993 or 1994, many generations of deliberate hybrids were raised, selecting promising parents from his collection of previous unnamed seedlings which had been raised during the breeding program. The inventor selected 'WALSNOWRUF' in 2003 or 2004. The intermediate and immediate parents of 'WALSNOWRUF' are unknown to the inventor and have not been retained. Thus, no parental comparison information is available.

Asexual propagation of 'WALSNOWRUF' was first accomplished by the inventor in 2003 or 2004 using semi-ripe shoot cuttings. Since that time, under careful observation, the distinguishing characteristics of 'WALSNOWRUF' have been determined stable and uniform, and to reproduce true to type in successive generations of asexual propagation via semi-ripe shoot cuttings.

SUMMARY OF THE NEW VARIETY

The distinguishing characteristics of 'WALSNOWRUF' are listed below. 'WALSNOWRUF' has not been tested under all possible conditions and phenotypic differences may be observed with variations in environmental, climatic, and cultural conditions.

1. Plants of 'WALSNOWRUF' exhibit a compact mounding growth habit.
2. The foliage of 'WALSNOWRUF' is glossy evergreen in color.
3. 'WALSNOWRUF' bears large double flowers in a crisp white color.
4. Plants of 'WALSNOWRUF' show good heat and humidity tolerance.
5. 'WALSNOWRUF' blooms profusely from April until June with occasional flowers present through summer and into early fall.
6. After two years of growth, plants of 'WALSNOWRUF' are 25 cm to 30 cm in height and 25 cm to 30 cm in width.
7. At maturity, 5 years, plants of 'WALSNOWRUF' are 30 cm to 40 cm in height and 30 cm to 40 cm in width.
8. 'WALSNOWRUF' prefers semi-shade in a moist, well drained, slightly acidic growing media.
9. 'WALSNOWRUF' is suitable for use as a garden specimen, landscape plants and as a container specimen.
10. 'WALSNOWRUF' is hardy to at least USDA Zone 7.

DESCRIPTION OF THE PHOTOGRAPHS

The accompanying color photographs illustrate the overall appearance of 'WALSNOWRUF' showing the colors of its foliage and flowers as true as it is reasonably possible to obtain in colored reproductions of this type. Both photographs were taken in May 2013 from one-year old plants which have been grown outdoors in 3-liter containers in the inventor's nursery in Arundel, West Sussex, United Kingdom.

BOTANICAL DESCRIPTION OF THE PLANT

Figure 1:
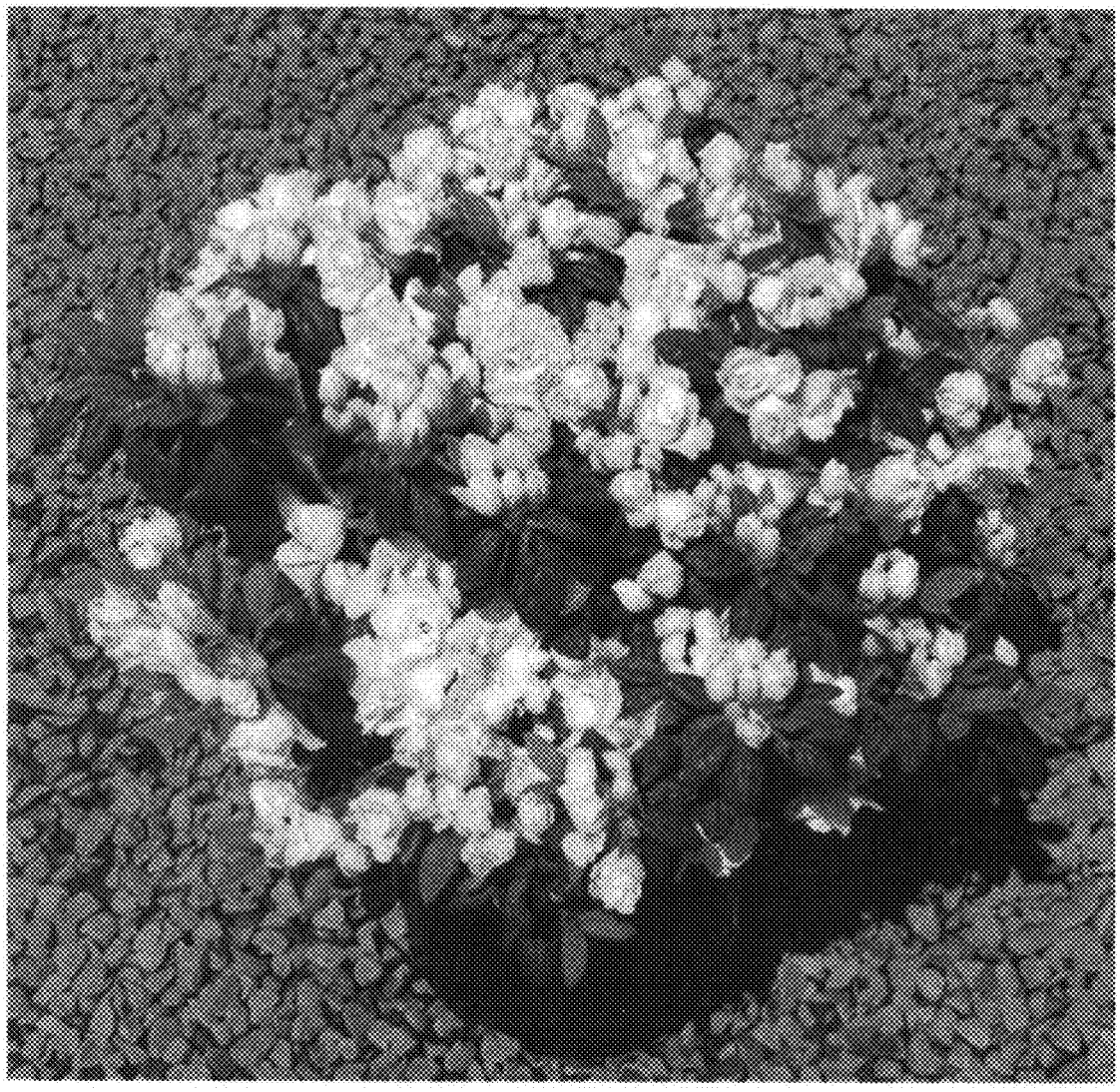
FIG. 1 depicts a whole plant of 'WALSNOWRUF'.
Figure 2:
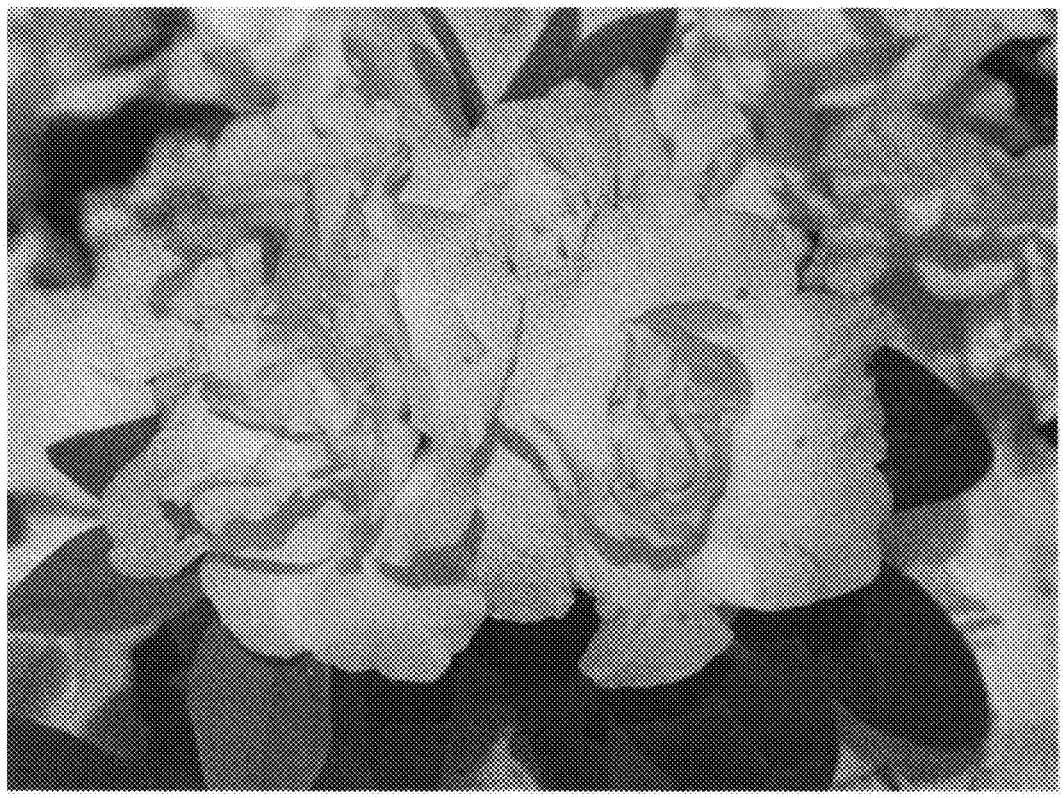
FIG. 2 depicts a close-up view of the flower of 'WALSNOWRUF'.

The following is a detailed description of 'WALSNOWRUF'. The observed plant was 2-years old and was growing out of doors in a 1-gallon container in Santa Barbara, Calif. where the botanical description was made in May 2014. The color determinations are in accordance with the 2007 edition of The Colour Chart of the Royal Horticultural Society, London, England, except where general color terms of ordinary dictionary significance are used. Growing conditions are similar to those of other *Rhododendron.*

Botanical classification:

*Family.*—Ericaceae.

*Genus.*—*Rhododendron.*

*Species.*—*kaempferi* hybrid.

*Cultivar.*—'WALSNOWRUF'.

Parentage: Un-named seedlings raised during the breeding program; parents not retained or described.

Plant:

*Commercial classification.*—Perennial.

*Common name.*—Evergreen azalea.

*Use.*—Ornamental for container or landscape.

*Cultural requirements.*—Plant in partial shade and any free-draining slightly acidic soil.

*Particular pest resistance or susceptibility.*—None observed.

*Propagation method.*—Semi-ripe cuttings without use of rooting hormone.

*Rooting system.*—Fine and fibrous.

*Time to initiate roots.*—Roots begin to form after 5 to 8 weeks; a further 5 weeks are required for the plant to be well-rooted.

*Vigor.*—Moderately vigorous; lateral branching is encouraged by pinching.

*Habit.*—Low mound.

*Dimensions after two years.*—25 cm to 30 cm in height and 25 cm to 30 cm in width.

*Dimensions after five years.*—30 cm to 40 cm in height and 30 cm to 40 cm in width.

*Hardiness.*—USDA Zone 7.

Stem:

*Dimensions.*—Length 1.5 cm (height of manual pinch); diameter at base: 1 cm.

*Shape.*—Cylindrical.

*Bark.*—Rough, color 177A.

*Number of branches.*—12.

Branches (current season extension growth):

*Shape.*—Cylindrical.

*Surface.*—Sparsely pubescent.

*Dimensions.*—Length: 18 cm to 20 cm, diameter 3 mm.

*Color.*—144B.

*Internode length* (*range*).—1.0 cm to 1.5 cm.

Branches (previous year's growth):

*Shape.*—Cylindrical.

*Dimensions.*—Length: 15 cm to 20 cm, diameter 3 mm.

*Color.*—172A.

*Bark surface.*—Rough.

*Internode length* (*range*).—1.0 cm to 2.0 cm.

Foliage:

*Type.*—Evergreen.

*Leaf arrangement.*—Alternate.

*Leaf division.*—Simple.

*Leaf dimensions* (*average, fully developed*).—6 cm in length and 3 cm in width.

*Leaf color* (*current season new growth, adaxial surface*).—141B.

*Leaf color* (*current season new growth, abaxial surface*).—143C.

*Leaf color* (*mature, previous year's growth, adaxial surface*).—136A.

*Leaf color* (*mature, previous year's growth, abaxial surface*).—138A.

*Leaf shape.*—Elliptic, base cuneate, apex obtuse.

*Leaf margin.*—Ciliate, hairs fine, 1 mm, silver-gray 156D.

*Leaf surface* (*both surfaces*).—Smooth, glossy, sparsely pubescent, hairs fine, 1 mm, silver-gray 156D.

*Venation.*—Pinnate, color 141B.

*Petioles.*—Dimensions: 5 mm in length, 1.5 mm to 2.0 mm in width. Color: 144A.

Inflorescence:

*Inflorescence type.*—Terminal.

*Flower arrangement.*—Flowers in groups of 8 to 12.

*Flower aspect.*—Upward or outward.

*Form.*—Rotate.

*Inflorescence quantity.*—Ranges between 3 and 5 per branch and between 30 and 50 at peak of flowering.

*Dimensions of inflorescence* (*average*).—10 cm in diameter, 8 cm in depth.

*Blooming season.*—Early summer through early fall (July to September approximately).

*Lastingness of flowers* (*on the plant*).—7 to 10 days.

Bud:

*Arrangement.*—Borne in clusters of 8 to 12 buds; initially, each bud is sheathed by a pair of modified leaf bracts which fall away as the bud swells.

*Bud shape.*—Ovoid.

*Dimensions* (*immediately prior to opening*).—12 mm in length and 10 mm in diameter.

*Bracts* (*bud sheath*).—Pair, each 18 mm in length, 15 mm in width.

*Bracts* (*bud sheath*).—Shape cupped, texture paper-like, base truncate, apex acute.

*Bract color* (*adaxial surface*).—Base 155C, becoming 142C and 142B at apex; in addition, dorsal (convex) surface 163A.

*Bract color* (*abaxial surface.*—Base 155C, becoming 142C and 142B at apex.

*Bud color* (*as bracts fall away, as bud opens*).—149D.

*Sepals.*—5 in number, fused at base.

*Sepal color* (*both surfaces*).—144A, surface pubescent, hairs fine, 1 to 2 mm, silver-gray 156D.

*Sepal dimensions.*—Length: 7 mm; width: 5 mm.

*Sepal shape.*—Ovate, base rounded, apex cuspidate.

*Sepal surface.*—Pubescent, many fine hairs 1 mm to 2 mm, silver-gray 156D.

*Sepal margin.*—Entire.

*Pedicel.*—Length 14 mm, width 2 mm.

*Pedicel surface.*—Pubescent, many fine hairs 1 mm to 2 mm, color 144A.

Flowers:

*Form*.—Semi-double, initially cylindrical, becoming globose.

*Flowering period*.—Flowering commences in April and is profuse until June; occasional flowers are produced until July or September.

*Fragrance*.—None.

*Flower retention*.—Flowers are persistent.

*Flower dimensions* (*including corolla tube*).—5.5 cm to 6.0 cm in diameter, 3.0 cm in depth.

*Corolla tube dimensions*.—2.5 cm in length; 0.5 cm to 1.0 cm in diameter, narrowest at the base.

*Petal arrangement*.—Three whorls, each whorl consisting of 5 petals fused at base; inner whorl occasionally modified to anther-bearing petaloid stamens.

*Petal shape*.—Widely ovate, base truncate, apex rounded.

*Petal dimensions*.—Outer whorl: 35 mm in length, 25 mm in width. Second whorl: 28 mm in length, 22 mm in width. Inner whorl: 25 mm in length, 20 mm in width.

*Petal margin*.—Smooth, gently ruffled.

*Petals*.—Color (both surfaces): White (whiter than NN155D), base 150C. Spots: Occasionally present on adaxial surface as short dashes towards petal base, length 1 mm to 2 mm, width 0.5 mm to 1.0 mm, color 150C. Surface: Smooth, glossy.

*Venation*.—Parallel, color 136A.

*Peduncle*.—Dimensions: 5 mm in length, 2 mm in width, ribbed. Dimensions: Approximately 45 degrees from the stem. Surface: Smooth. Color: N144D.

Reproductive organs:

*Petaloid stamens* (*when so modified*).—1 to 9 in number, length: 25 mm, width 20 mm, color white, (whiter than NN155D).

*Anthers*.—Shape is oblong, bifid, length 3 mm, width 1.0 mm to 1.5 mm, color 167D.

*Pollen*.—Absent.

*Pistil*.—One, length is 5 mm, diameter 0.5 mm, color 138C.

*Style*.—2.5 cm to 3.0 cm in length; initially light green becoming white NN155D.

*Stigma*.—Color 137B; shape is rounded.

*Ovary*.—Ovate, 4 mm in length, 3 mm in diameter; surrounded by dense very fine silver-gray hairs, length 5 mm, color nearest 156D.

Seed set: None observed.

COMPARISON WITH COMMERCIAL VARIETY

'WALSNOWRUF' may be compared with Azalea 'Honesty' (U.S. Plant Pat. No. 12,054) which also bears double pure white flowers. 'Honesty' is a florist or greenhouse azalea and is not hardy, whereas 'WALSNOWRUF' has been observed to tolerate temperatures as low as −15° C. (USDA Hardiness Zone 7). In addition, the flowers of 'Honesty' are very large, up to 9 cm in diameter, whereas the flowers of 'WALSNOWRUF' are typically 5.5 cm to 6.0 cm in diameter.

In addition, 'WALSNOWRUF' may be compared with Azalea 'April Gem' (unpatented) which is a white double-flowered Mehlquist hardy hybrid. The flowers of 'April Gem' are borne singly or in clusters of 2 to 4 flowers whereas the flowers of 'WALSNOWRUF' are arranged in large clusters, typically between 8 and 12 flowers per inflorescence. Finally, the flowers of 'April Gem' are smaller (diameter 4 cm to 5 cm) than the flowers of 'WALSNOWRUF', and are generally described as slightly fragrant whereas no fragrance has been observed in 'WALSNOWRUF'.

I claim:

1. A new and distinct variety of *Rhododendron* plant named 'WALSNOWRUF' as described and illustrated herein.

* * * * *